US008546574B2

(12) United States Patent
Cohen et al.

(10) Patent No.: US 8,546,574 B2
(45) Date of Patent: Oct. 1, 2013

(54) CONGLOMERATES OF TENATOPRAZOLE POTASSIUM SALTS

(75) Inventors: Avraham Cohen, Tel-Aviv (IL); François Schutze, Saint-Nom-la-Breteche (FR); Suzy Charbit, Creteil (FR); Stéphane Bernad, La Varenne Saint-Hilaire (FR); Guillaume Tauvel, Rouen (FR); Marie-Noëlle Petit, Mont Saint-Aignan (FR); Gérard Coquerel, Boos (FR)

(73) Assignee: Sidem Pharma SA, Luxembourg (LU)

( * ) Notice: Subject to any disclaimer, the term of this patent is extended or adjusted under 35 U.S.C. 154(b) by 528 days.

(21) Appl. No.: 12/448,055

(22) PCT Filed: Dec. 3, 2007

(86) PCT No.: PCT/FR2007/001981
§ 371 (c)(1),
(2), (4) Date: Nov. 23, 2010

(87) PCT Pub. No.: WO2008/081104
PCT Pub. Date: Jul. 10, 2008

(65) Prior Publication Data
US 2011/0060002 A1  Mar. 10, 2011

(30) Foreign Application Priority Data
Dec. 4, 2006 (FR) ..................... 06 10553

(51) Int. Cl.
*C07D 471/04* (2006.01)
*A61K 31/444* (2006.01)
*A61P 1/04* (2006.01)

(52) U.S. Cl.
USPC .......................... 546/118; 514/303

(58) Field of Classification Search
USPC ......................... 546/118; 514/303
See application file for complete search history.

(56) References Cited

U.S. PATENT DOCUMENTS

| 4,808,596 A | 2/1989 | Matsuishi et al. ............. 514/303 |
| 2006/0122216 A1 | 6/2006 | Yamashita ................... 514/303 |
| 2007/0179176 A1 | 8/2007 | Cohen et al. ................. 514/303 |

FOREIGN PATENT DOCUMENTS

| EP | 0254588 | 1/1988 |
| EP | 1664044 | 6/2006 |
| FR | 2710337 | 3/1995 |
| WO | 2004074285 | 9/2004 |
| WO | 2006/043280 | * 4/2006 |
| WO | WO 2006043280 A1 | 4/2006 |

OTHER PUBLICATIONS

International Search Report—Jul. 4, 2008.
Towards a Grammar of Crystal Packing dated Apr. 22, 1994.
Preferential Crystallization dated Nov. 4, 2006.

* cited by examiner

*Primary Examiner* — Niloofar Rahmani
(74) *Attorney, Agent, or Firm* — Sofer & Haroun, LLP

(57) ABSTRACT

The invention relates to conglomerates of tenatoprazole potassium salts of the following general formula (I), that consist of an equimolar mixture of enantiomers having R and S configurations and capable of crystallization in the form of a conglomerate, wherein said salts are selected from tenatoprazole dehydrated potassium salt, tenatoprazole potassium dimethanolate, tenatoprazole potassium diethanolate and tenatoprazole potassium ethylene-glycolate. The invention also relates to a pharmaceutical composition containing such salt, and to the use of said salt.

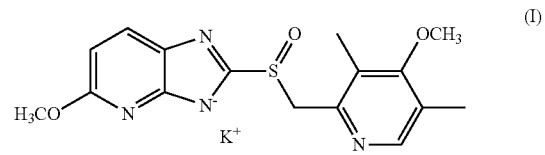

(I)

7 Claims, No Drawings

CONGLOMERATES OF TENATOPRAZOLE POTASSIUM SALTS

RELATED APPLICATIONS

This application is a National Phase application of PCT/FR2007/001981, filed on Dec. 3, 2007, which in turn claims the benefit of priority from French Patent Application No. 06 10553, filed on Dec. 4, 2006, the entirety of which are incorporated herein by reference.

FIELD OF THE INVENTION

The present invention relates to tenatoprazole salts and more particularly to tenatoprazole potassium salts that crystallize in the form of conglomerates, and also to their use for forming a sodium salt of one or other of the tenatoprazole enantiomers.

DESCRIPTION OF RELATED ART

Tenatoprazole, or 5-methoxy-2-[[(4-methoxy-3,5-dimethyl-2-pyridyl)methyl]sulfinyl]imidazo[4,5-b]pyridine, described in patent EP 254 588, is included among medicaments considered as being proton-pump inhibitors having the effect of inhibiting gastric secretion, and it may be used more particularly in the treatment of gastro-esophageal reflux, digestive hemorrhaging and dyspepsia.

It may be represented by the following general formula:

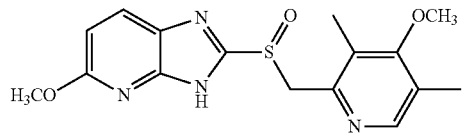

This compound has asymmetry at the sulfur atom and may thus be in racemic form or in the form of one or other of its two enantiomers. These enantiomers, like the racemic mixture, may conventionally be used in the form of salts, such as the magnesium, potassium or sodium salts, which are generally easier to manipulate than the corresponding acid form.

Recent studies have shown that, unlike all the other proton-pump inhibitors, for instance omeprazole or lansoprazole, tenatoprazole has a markedly longer duration of action, resulting from a plasmatic half-life that is about seven times greater. Thus, the collected medical data show that tenatoprazole provides a greater level of relief of the symptoms and of cicatrization of gastric lesions than that of the other known medicaments belonging to the same therapeutic class of proton-pump inhibitors, which thus allows its efficacious use in the treatment of atypical and esophageal symptoms of gastro-esophageal reflux, digestive hemorrhaging and dyspepsia, as indicated hereinabove.

Furthermore, it has been shown that each of the (+) and (−), or R and S enantiomers, respectively, contributes differently toward the properties of tenatoprazole, and that S-tenatoprazole has pharmacokinetic properties that are significantly different than those of the racemic mixture and of the other enantiomer of R configuration.

In particular, the studies forming the subject of patent EP 1 664 044 have shown that S-tenatoprazole sodium salt monohydrate has unexpected properties that distinguish it from S-tenatoprazole itself, and from other proton-pump inhibitors, and more particularly excellent solubility that facilitates the pharmaceutical implementation methods and significantly improves the absorption and the therapeutic efficacy of the medicament containing it.

Patent application WO 2004/074285 describes R-tenatoprazole and a process for preparing it.

The S-tenatoprazole sodium salt described in patent EP 1 664 044 may be prepared via two different processes.

The first preparation process consists in reacting sodium hydroxide with S-tenatoprazole obtained by resolution of the racemic mixture, at a temperature of between 50 and 70° C., and then in precipitating the salt obtained after removing the solvent.

The second process consists succinctly in performing an enantioselective oxidation of the corresponding sulfide by means of an oxidizing agent, in the presence of a vanadium- or titanium-based catalyst and a suitable chiral ligand, and then in performing a salification with sodium hydroxide.

The use of one or other of these processes gives satisfactory results in terms of enantiomeric excess and yield. However, it remains necessary to find novel routes for synthesizing the tenatoprazole enantiomers, which not only afford excellent results as regards the yield and the selectivity, but also use a minimum amount of toxic substance, or even no toxic substance, in order to limit the risks associated with the use of substances that are harmful to health and to the environment.

The inventors have thus sought to obtain compounds from which novel synthetic routes satisfying the criteria mentioned above may be envisioned.

Extensive studies have enabled them to develop novel tenatoprazole potassium salts, which have a particular crystal form, and to show that these salts can be used not only in this form in the therapeutic field, but also, advantageously, for the preparation of the sodium salt of the tenatoprazole enantiomers of S and R configuration, the therapeutic advantages of which have been described hereinabove.

OBJECTS AND SUMMARY

One subject of the invention is thus tenatoprazole potassium salts, represented by the following general formula:

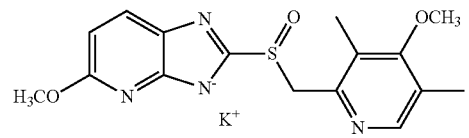

These salts are formed from an equimolar mixture of enantiomers of R and S configuration, crystallizing in the form of conglomerates, said salts being chosen from tenatoprazole potassium salt dihydrate, potassium tenatoprazole dimethanolate, potassium tenatoprazole diethanolate and potassium tenatoprazole ethylene glycolate.

The term "conglomerate" means a racemic mixture which, in a given solvent and within a certain temperature range, is formed from two types of crystal that each contain only molecules of the same configuration, possibly incorporating solvent molecules. If solvent molecules are incorporated, they are then referred to as "solvates". Hydrates are solvates in which the solvent is water.

Crystallization of the tenatoprazole potassium salts of the invention in the form of a conglomerate means that the crystal stacking allows spontaneous discrimination of the S and R enantiomers during the crystallization. However, it should be noted that it is impossible to predict whether a racemic mixture will crystallize in the form of a conglomerate, and it is impossible to predict the type of stacking of a phase. It is also known that about 5% of racemic mixtures crystallize in the form of conglomerates (C. P. Brock et al., Chem. Mater., 1994, 6, pp. 1118-1127). Thus, tenatoprazole in acid form crystallizes in the form of a racemic mixture, as does its sodium salts.

It has also been shown that the production of a conglomerate is a necessary but insufficient condition for resolution by preferential crystallization (G. Coquerel, *Preferential Crystallization in Topic in Current Chemistry*, Novel Optical Resolution Technologies, Springer, Berlin-Heidelberg, Eds K. Sakai, N. Hirayama and R. Tamura, 2007, 269, 1-51).

The characteristics of the compounds according to the invention are specified hereinbelow.

When the salt is formed from tenatoprazole potassium salt dihydrate, it produces an X-ray diffraction spectrum comprising lines at the following inter-reticular distances: 15.16; 8.07; 7.59; 7.23; 7.02; 5.72; 5.55; 5.41; 5.32; 5.05; 4.51; 4.35; 4.29; 4.22; 4.061; 3.926; 3.748; 3.624; 3.539; 3.487; 3.436; 3.392; 3.292; 3.252; 3.222; 3.102; 3.034 (in Angströms).

When the salt is a solvate formed from potassium tenatoprazole dimethanolate, it produces an X-ray diffraction spectrum comprising lines at the following inter-reticular distances: 13.79; 6.87; 5.64; 5.44; 4.83; 4.57; 4.31; 3.97; 3.921; 3.865; 3.794; 3.644; 3.56; 3.508; 3.431; 3.393; 3.309; 3.233; 3.116 (in Angströms).

When the salt is a solvate formed from potassium tenatoprazole diethanolate, it produces an X-ray diffraction spectrum comprising lines at the following inter-reticular distances: 13.79; 10.73; 9.41; 7.75; 6.87; 6.71; 6.40; 6.25; 5.97; 5.463; 5.377; 5.128; 4.918; 4.711; 4.562; 4.418; 4.020; 3.936; 3.892; 3.855; 3.705; 3.656; 3.623; 3.573; 3.508; 3.460; 3.446; 3.363; 3.302; 3.249; 3.167; 3.129; 3.102; 3.043 (in Angströms).

When the salt is a solvate formed from potassium tenatoprazole ethylene glycolate, it produces an X-ray diffraction spectrum comprising lines at the following inter-reticular distances: 12.92; 9.30; 7.89; 7.59; 6.77; 6.05; 5.828; 5.604; 5.409; 5.026; 4.907; 4.657; 4.569; 4.478; 4.295; 4.178; 4.013; 3.972; 3.931; 3.798; 3.692; 3.650; 3.608; 3.543; 3.396; 3.340; 3.300; 3.271; 3.204; 3.148; 3.105; 3.060; 3.013 (in Angströms).

A subject of the invention is also a pharmaceutical composition comprising a tenatoprazole potassium salt, the characteristics of which have been described hereinabove, combined with one or more pharmaceutically acceptable supports or excipients.

Another subject of the present invention is the use of such a potassium salt for the preparation of an enantiomerically pure tenatoprazole sodium salt.

The preparation of the enantiomerically pure tenatoprazole sodium salt is advantageously performed by resolving the optical enantiomers of one of the racemic potassium salts, according to a preferential crystallization process, followed by converting one of said optical enantiomers of the potassium salt into the corresponding enantiomers of the sodium salt.

A preferential crystallization process is especially described in patent FR 2 710 337. This process allows alternate crystallization of the two chiral R and S compounds from the corresponding thermodynamically stable conglomerate. This technique has many advantages:

it avoids the use of an intermediate chiral agent, whose synthesis and recovery make the process more complex;
the two optical antipodes are each obtained directly;
the yield may be considered as quantitative for each enantiomer as a result of successive recycling of the mother liquors;
purification of the crude enantiomer crystals obtained is easy.

In the case of tenatoprazole, this process consists generally in performing the following successive steps:

(i) dissolution of racemic tenatoprazole acid and of potassium hydroxide KOH in a solvent or in a mixture of solvents chosen from water, methanol, ethanol and ethylene glycol. During this step, and on account of the incongruent solubility of these salts, it is preferable to use an excess of KOH relative to the number of equivalents of tenatoprazole, for example an excess of between 10% and 30%;

(ii) crystallization of the potassium salt either by evaporating the solvent, or by lowering the temperature of the system, so as to obtain the tenatoprazole potassium salt in the form of a conglomerate;

(iii) determination of the homogenization temperature of the racemic mixture, known as $T_L$:

(iv) addition of a small amount of enantiomerically pure tenatoprazole acid with potassium hydroxide;

(v) determination of the homogenization temperature of the system, known as $T_{HOMO}$;

(vi) selection of the initial temperature of the system, known as $T_I$, for the start of the resolution process, such that $T_I > T_{HOMO}$;

(vii) lowering of the temperature down to the resolution end temperature, known as $T_F$, either by applying a temperature ramp, or by quenching;

(viii) addition of the chosen enantiomerically pure potassium salt, at the temperature known as $T_E$, so as to seed the system. The amount of salt added is about 1% of the expected harvest. When the temperature reduction of step (vii) has been performed by applying a temperature ramp, this gives $T_{HOMO} > T_E \geq T_F$. When the temperature reduction has been performed by quenching, this gives $T_E = T_F$.

During the cooling, the enantiomer in excess crystallizes (via a twofold mechanism of secondary germination and growth), whereas the enantiomer in deficit experiences a delay in primary germination and thus remains supersaturated. The depletion of the solution is monitored by polarimetric analysis.

(ix) filtration of the system at a temperature known as $T_F = T_{FILTRATION}$, when the optical antipode begins to nucleate, preferably slightly before germination of the antipode, in other words when the derivative of the curve of the polarimetric monitoring changes sign.

By compensation with solvent and with racemic mixture, the system is then placed in a symmetrical position relative to the initial situation, so as to be ready, where appropriate, for separation of the second enantiomer.

It is then possible to repeat recycling of mother liquor and to add masses of racemic mixture equivalent to that of the enantiomer harvested in the preceding filtration. If the first crystallization allowed the (S) enantiomer to be isolated, each odd and even operation gives, respectively, the (S) and (R) enantiomers. In this way, a quantity 2Q of racemic mixture can be resolved into two masses Q of enantiomers of very high purity since the presence of a stable conglomerate also makes it possible to optimally purify the crude harvests obtained from the preferential crystallizations.

The starting racemic mixture (step (i)) may be obtained via the known processes, for example according to the process described in patent EP 254 588. Thus, it may be prepared by treating with an oxidizing agent, such as a perbenzoic acid, the corresponding sulfide originating from the condensation of a thiol and of a pyridine. The reaction preferably takes place in the presence of a base such as potassium hydroxide in a suitable solvent, for example hot ethanol.

The enantiomerically pure potassium salt added in step (viii) may be obtained from the racemic mixture, via well known techniques, using a suitable separation method, for example by preparative column chromatography, for instance chiral chromatography or HPLC, followed by salification and preparation of the corresponding solvate, or via a process as described in Examples 5 to 8.

A potassium salt according to the invention, on account of its inhibitory properties on gastric acid secretion, may be used in its native form in a pharmaceutical composition intended for treating gastrointestinal complaints, and more particularly for treating gastric and duodenal ulcers, gastro-esophageal reflux, digestive hemorrhaging and dyspepsia. In accordance with the present invention, it may also be used for the preparation of S-tenatoprazole sodium salt or R-tenatoprazole sodium salt.

The conversion of one of the optical enantiomers of the potassium salt into the corresponding enantiomer of the sodium salt may be performed via known processes, for example using ion-exchange resins such as zeolites, or by crystallization of free acid and salifying it with sodium hydroxide.

S-Tenatoprazole sodium salt obtained as indicated hereinabove may itself advantageously be used in the manufacture of a medicament for treating digestive pathologies in which inhibition of acid secretion must be intense and prolonged, or, in the case of patients under multidrug treatment, for the treatment of digestive pathologies, gastro-esophageal reflux and digestive hemorrhaging that are resistant to the other proton-pump inhibitors.

It may also be used for the manufacture of a medicament that affords a significant improvement in cicatrization and also an increase in the speed of normalization of the histological changes in gastric and esophageal lesions in man or animals, and consequently a large reduction in relapses.

The S-tenatoprazole sodium salt obtained from the compounds according to the invention may also be used for the manufacture of a medicament with improved pharmacokinetic properties allowing a dosage of a single daily intake of medicament in pertinent indications, in particular for eradicating *Helicobacter pylori* in the treatment of duodenal ulcers, which require two intakes, morning and evening, with the other proton-pump inhibitors.

DETAILED DESCRIPTION

The examples that follow are intended to illustrate the invention without, however, limiting its scope.

Examples 1 to 4 relate to the preparation of the racemic compounds according to the Invention.

Examples 5 to 8 relate to the preparation of the enantiomerically pure corresponding compounds, which are used for seeding the system during the process of resolution by preferential crystallization of the compounds according to the invention.

Examples 9 to 13 describe the experimental conditions used for performing the processes of resolution of compounds according to the invention via preferential crystallization, and also the results obtained. In these examples, the temperature reduction in step (vii) is achieved by applying a temperature ramp. The optical purities were measured by polarimetry at a wavelength $\lambda=546$ nm with a concentration of about 20 mg/L.

Example 14 describes the crystal structure of enantiomerically pure potassium salts.

Examples 15 to 18 are comparative examples intended to show that the use of solvents (such as isopropyl alcohol, an ethanol/propylene glycol mixture, an ethanol/water mixture or an N-methylpyrrolidinone/water mixture) other than those used in the process according to the invention (i.e. methanol, ethanol, water or ethylene glycol) do not give the expected results, since they do not make it possible to obtain crystals in the form of conglomerates.

Example 19 relates to the use of compounds according to the invention for the preparation of enantiomerically pure tenatoprazole sodium salt.

Experimental Device

The experimental device used for the experiments described in Examples 9 to 12 is identical except for the reactor, the size and shape of which vary as a function of the volume of the system.

The operations are performed alternatively in two ground-necked (29/32 No. 4) tubes about 12 cm long and 29 mm in diameter for Example 9. For Examples 10 and 11, the tube dimensions are about 20 cm in length and 5 cm in diameter with a ground neck (29/32 No. 4).

These tubes are equipped, in their upper part, with a side tube for establishing a negative pressure necessary during the filtration. The crystals are recovered on a No. 2 or 3 sinter funnel adaptable onto each tube via a rubber ring. Stirring is performed with a magnetic bar. The liquors pass successively from one tube to the other. These transfers, which are minimized, do not prevent losses between each operation. The smaller the amounts of product used, the greater proportionately will be the losses. These losses may be listed in two categories:

losses, on the sinter funnel and in the initial tube, of mother liquor containing the enantiomeric excess of the end of crystallization. Compensation is performed by adding racemic crystals and solvent;

losses of solvent mainly due to the filtration created by the negative pressure. Compensation is performed by adding additional solvent to each operation.

In certain cases, for example when a very volatile solvent is used, the compensation process must be more precise. A small amount of the solution is taken, in order to determine its composition, enabling thereafter a rigorous compensation.

In order to achieve good reproducibility of the results, the heat-exchange fluid circulating in the jacket is temperature regulated with a precision of ±0.1° C. The apparatus used makes it possible to set a reproducible cooling law.

In Example 12, the operations are performed in a thermostatically regulated jacketed 2-liter reactor. Stirring is mechanical and is performed using a twin-blade paddle. Filtration takes place using a centrifuge equipped with a sock 20 cm in diameter and 10 cm long, and for which the pore diameter of the Nylon filtering medium is 20 µm, the mother liquor recovered in a container being transferred into the reactor.

Example 1

Preparation of Racemic Tenatoprazole Potassium Salt Dihydrates

Examples 1a to 1c describe three different processes for the preparation of racemic tenatoprazole potassium salt dihydrates according to the invention.

Example 1a 0.99 g (i.e. 17.6 mmol) of potassium hydroxide (KOH) is dissolved in 5 mL of water. 5.14 g (i.e. 14.9 mmol) of racemic tenatoprazole acid are added to the solution. The dissolution is rapid. After stirring for 12 hours at 0° C., a crystalline product is filtered off on a Büchner funnel. The crystalline product is analyzed by X-ray powder diffraction.

Example 1b 0.22 g (i.e. 3.9 mmol) of potassium hydroxide is dissolved in 30 mL of methanol, and 1.13 g (i.e. 3.3 mmol) of racemic tenatoprazole acid are then added to the solution. The dissolution is rapid. After a few minutes, the crystalline product appears. This product is filtered off on a Büchner tunnel, dried and then analyzed by X-ray powder diffraction.

Example 1c 0.23 g (i.e. 4.1 mmol) of potassium hydroxide is dissolved in 30 mL of ethanol, and 1.23 g (i.e. 3.6 mmol) of racemic tenatoprazole acid are then added to the solution. The dissolution is rapid. After a few minutes, the crystalline product appears. This product is filtered off on a Büchner funnel, dried and then analyzed by X-ray powder diffraction.

Example 2

Preparation of Racemic Tenatoprazole Potassium Salts Solvated with Methanol 0.11 g (i.e. 1.96 mmol) of potassium hydroxide is dissolved in 15 mL of pure methanol, and 0.58 g (i.e. 1.7 mmol) of racemic tenatoprazole acid is then added to the solution. Dissolution is rapid. After a few minutes, the crystalline product appears. This product is filtered off by gravity on filter paper, followed by wet analysis of a stock solution by X-ray powder diffraction in a chamber whose atmosphere is saturated with methanol.

Example 3

Preparation of Racemic Tenatoprazole Potassium Salts Solvated with Ethanol 0.23 g (i.e. 4.1 mmol) of potassium hydroxide is dissolved in 30 mL of ethanol, and 1.23 g (i.e. 3.6 mmol) of racemic tenatoprazole acid are then added to the solution. Dissolution is rapid. After a few minutes, the crystalline product appears. This product is filtered off by gravity on filter paper, followed by wet analysis of a stock solution by X-ray powder diffraction in a chamber whose atmosphere is saturated with ethanol.

Example 4

Preparation of Racemic Tenatoprazole Potassium Salts Solvated with Ethylene Glycol Examples 4a and 4b describe two different processes for the preparation of racemic tenatoprazole potassium salts solvated with ethylene glycol.

Example 4a 0.3 g (i.e. 5.4 mmol) of potassium hydroxide is dissolved in a solvent mixture composed of 20 mL of ethanol and 2 mL of ethylene glycol, and 1.54 g (i.e. 4.5 mmol) of racemic tenatoprazole acid are then added to the solution. Dissolution is rapid. After stirring for a few hours, the crystalline product appears. This product is filtered off on a Büchner funnel, dried and then analyzed by X-ray powder diffraction.

Example 4b 0.2 g (i.e. 3.6 mmol) of potassium hydroxide is dissolved in a solvent mixture composed of 10 mL of methanol and 15 mL of ethylene glycol, and 1.03 g (i.e. 3 mmol) of racemic tenatoprazole acid are then added to the solution. Dissolution is rapid. After stirring for a few hours at 0° C., the crystalline product appears. This product is filtered off on a Büchner funnel, dried and then analyzed by X-ray powder diffraction.

Example 5

Preparation of Enantiomerically Pure Tenatoprazole Potassium Salt Dihydrates

Examples 5a to 5c describe three different processes for the preparation of enantiomerically pure tenatoprazole potassium salt dihydrates.

Example 5a 0.26 g (i.e. 0.75 mmol) of acid tenatoprazole of S configuration is dissolved in 14 g of ethanol, in the presence of 0.05 g (i.e. 0.89 mmol) of KOH and 10 drops of water. After partial evaporation of the solvent, the product is filtered off on a Büchner funnel and left in the open air; the diethanolate initially formed undergoes a rapid and total conversion into dihydrate.

Example 5b 2.7 g (i.e. 7.8 mmol) of acid tenatoprazole of S configuration are dissolved in 23 g of dioxane, in the presence of 1.8 mg of a 5.1 mol.L$^{-1}$ potassium hydroxide solution (i.e. 9.2 mmol). After partial evaporation of the solvent, the product is filtered off on a Büchner funnel and analyzed by X-ray powder diffraction.

Example 5c 0.15 g (i.e. 0.43 mmol) of acid tenatoprazole of S configuration is dissolved in 3.9 g of tetrahydrofuran, in the presence of 0.1 mL of an aqueous 4.75 mol.L$^{-1}$ potassium hydroxide solution (i.e. 0.48 mmol). After slow evaporation of the solvent, the product is analyzed by X-ray powder diffraction.

Example 6

Preparation of Enantiomerically Pure Tenatoprazole Potassium Salts Solvated with Methanol 0.3 g (i.e. 5.4 mmol) of potassium hydroxide is dissolved in 10 mL of methanol, and 1.53 g (i.e. 4.4 mmol) of acid tenatoprazole of S configuration are then added to the solution. Dissolution is rapid. After a few minutes, the crystalline product appears. This product is filtered off by gravity on filter paper, followed by wet analysis of a stock solution by X-ray powder diffraction in a chamber whose atmosphere is saturated with methanol.

Example 7

Preparation of Enantiomerically Pure Tenatoprazole Potassium Salts Solvated with Ethanol 0.22 g (i.e. 3.9 mmol) of potassium hydroxide is dissolved in 30 mL of ethanol, and 1.13 g (i.e. 3.3 mmol) of acid tenatoprazole of S configuration are then added to the solution. Dissolution is rapid. After a few minutes, the crystalline product appears. This product is filtered off by gravity on filter paper, followed by wet analysis of a stock solution by X-ray powder diffraction in a chamber whose atmosphere is saturated with ethanol.

Example 8

Preparation of Enantiomerically Pure Tenatoprazole Potassium Salts Solvated with Ethylene Glycol Examples 8a to 8c describe three different processes for the preparation of enantiomerically pure tenatoprazole potassium salts solvated with ethylene glycol.

Example 8a 0.09 g (i.e. 1.6 mmol) of potassium hydroxide is dissolved in a solvent mixture composed of 3 mL of ethanol and 1 mL of ethylene glycol, and 0.48 g (i.e. 1.4 mmol) of acid tenatoprazole of S configuration is then added to the solution. Dissolution is rapid. After stirring for a few hours, the crystalline product appears. This product is filtered off on a Büchner funnel, dried and then analyzed by X-ray powder diffraction.

Example 8b 0.19 g (i.e. 3.4 mmol) of potassium hydroxide is dissolved in a solvent mixture composed of 4 mL of methanol and 1.5 mL of ethylene glycol, and 0.98 g (i.e. 2.8 mmol) of acid tenatoprazole of S configuration is then added to the solution. Dissolution is rapid. After stirring for a few hours at 0° C., the crystalline product appears. This product is filtered off on a Büchner funnel, dried and then analyzed by X-ray powder diffraction.

Example 8c 0.19 g (i.e. 3.4 mmol) of potassium hydroxide is dissolved in a solvent mixture composed of 5 mL of dioxane and 2 mL of ethylene glycol, and 1.1 g (i.e. 3.2 mmol) of acid tenatoprazole of S configuration are then added to the solution. Dissolution is rapid. After stirring for a few hours at 0° C., the crystalline product appears. This product is filtered off on a Büchner funnel, dried and then analyzed by X-ray powder diffraction.

Example 9

Resolution of the Ethanol Solvate of Tenatoprazole Potassium Salt by Preferential Crystallization, at a Scale of 50 cc in Ethanol Combined Conditions at Equilibrium
The table below shows the solubility of the racemic mixture of the potassium salt solvated with ethanol in an ethanolic potassium hydroxide solution such that the potassium hydroxide excess is about 0.2 molar equivalent relative to the potassium salt.

| Temperature (° C.) | 33.9 | 37 |
|---|---|---|
| Solubility (mass %) | 4.24 | 5.3 |

Variation of $T_{HOMO}$ with the Enantiomeric Excess
The results shown in the following table correspond to steps (iii) to (v).

| enantiomeric excess (% ee) | 0 | 3 | 6 | 9 | 11 |
|---|---|---|---|---|---|
| $T_{HOMO}$ (° C.) | $T_L$ = 33.9 | 34.8 | 35.2 | 35.5 | 35.7 |

Conditions Associated with the Kinetics
The conditions below are determined for use during steps (vi) to (ix)
Temperature $T_1$=38° C.>$T_{HOMO}$=35.7° C.
Seeding temperature=$T_E$=30° C.
Temperature $T_F$=19° C.
Temperature ramp=T=f(t)=38⅔*t (t in minutes) followed by a plateau at 19° C.

| Temperature (° C.) | 38 | 19 | 19 |
|---|---|---|---|
| t (min) | 0 | 30 | $T_{Filtration}$ |

Initial Conditions
Enantiomeric excess=11%

| Mass of ethanol | Mass of tenatoprazole acid (racemic) | Mass of tenatoprazole acid (configuration S) | Mass of KOH |
|---|---|---|---|
| 40 g / | 1.02 g<br>2.95 mmol | 0.125 g<br>0.36 mmol | 0.194 g<br>3.46 mmol |

Results

| No. | Mass of pure antipode (g) * | Optical purity (% ee) |
|---|---|---|
| 1 | 0.57 | −98.5 |
| 2 | 0.8 | +91.05 |
| 3 | 0.60 | −89 |
| 4 | 0.50 | +90.7 |
| 5 | 0.58 | −90.6 |
| 6 | 0.62 | +93.3 |
| Mean | 0.61 | 92.2 |

* Taking into account the efflorescence of the ethanol solvates of the potassium salts: the enantiomerically pure potassium salt used to seed the system is in the form of a suspension; the product harvested after filtration on a Büchner funnel undergoes a rapid and total conversion into dihydrate, which corresponds to the weighed mass.

Example 10

Resolution of the Methanol Solvate of Tenatoprazole Potassium Salt by Preferential Crystallization, at a Scale of 250 cc in Methanol Combined Conditions at Equilibrium
The table below shows the solubility of the racemic mixture of the potassium salt solvated in methanol in a methanolic potassium hydroxide solution such that the potassium hydroxide excess is about 0.2 molar equivalent relative to the potassium salt.

| Temperature (° C.). | 30 | 38 | 40 | 42 | 56 |
|---|---|---|---|---|---|
| Solubility (mass %) | 4.4 | 5.2 | 6.5 | 7.7 | 12.2 |

Variation of $T_{HOMO}$ with the Enantiomeric Excess

The results shown in the following table correspond to steps (iii) to (v)

| enantiomeric excess (% ee) | 0 | 1.85 | 3.69 | 6.26 | 9.9 |
|---|---|---|---|---|---|
| $T_{HOMO}$ (° C.) | 36 | 36.3 | 37 | 37.8 | 38.9 |

Conditions Associated with the Kinetics

The conditions below are determined for use during steps (vi) to (ix).

Temperature $T_I$=40>$T_{HOMO}$=38.9° C.
Temperature $T_E$=30° C.
Temperature $T_F$=20° C.
Temperature ramp=T=f(t)=40½*t (t in minutes) followed by a plateau at 20° C.

| Temperature (° C.) | 40 | 20 | 20 |
|---|---|---|---|
| t (min) | 0 | 40 | $T_{Filtration}$ |

Initial Conditions

Enantiomeric excess=10%

| Mass of methanol | Mass of tenatoprazole acid (racemic) | Mass of tenatoprazole acid (configuration S) | Mass of KOH |
|---|---|---|---|
| 250 g | 8.31 g | 0.83 g | 1.81 g |
| / | 24.0 mmol | 2.4 mmol | 32.3 mmol |

Results

| No. | Mass of pure antipode (g) * | Optical purity (%) |
|---|---|---|
| 1 | 1.69 | −70.9 |
| 2 | 1.38 | +53.3 |
| 3 | 1.7 | −57.1 |
| Mean | 1.59 | 60.4 |

* Taking into account the efflorescence of the ethanol solvates of the potassium salts: the enantiomerically pure potassium salt used to seed the system is in the form of a suspension; the product harvested after filtration on a Büchner funnel undergoes a rapid and total conversion into dihydrate, which corresponds to the weighed mass.

Example 11

Resolution of the Ethylene Glycol Solvate of Tenatoprazole Potassium Salt by Preferential Crystallization at a Scale of 200 cc in an Ethanol/Ethylene Glycol Mixture (80% VV-20% VV)

Combined Conditions at Equilibrium

The table below shows the solubility of the racemic mixture of the potassium salt solvated with ethylene glycol in an ethanol/ethylene glycol mixture (80% V-20% V) with a potassium hydroxide excess such that the potassium hydroxide excess is about 0.2 molar equivalent relative to the potassium salt.

| Temperature (° C.) | 28 | 32 | 34.5 | 39 |
|---|---|---|---|---|
| Solubility (mass %) | 20.3 | 24 | 25.6 | 33.5 |

Variation of $T_{HOMO}$ with the Enantiomeric Excess

The results shown in the following table correspond to steps (iii) to (v).

| enantiomeric excess (% ee) | 0 | 3 | 6 | 9 | 10.7 |
|---|---|---|---|---|---|
| $T_{HOMO}$ (° C.) | 34.4 | 34.9 | 35.4 | 35.9 | 36.2 |

Conditions Associated with the Kinetics

The conditions below are determined for use during steps (vi) to (ix).

Temperature $T_I$=40>$T_{HOMO}$=36.2° C.
Temperature $T_E$=30° C.
Temperature $T_F$=20° C.
Temperature ramp=T=f(t)=40½*t (t in minutes) followed by a plateau at 20° C.

| Temperature (° C.) | 40 | 20 | 20 |
|---|---|---|---|
| t (min) | 0 | 40 | $T_{Filtration}$ |

Initial Conditions

| Mass of ethanol | Mass of ethylene glycol | Mass of tenatoprazole acid (racemic) | Mass of tenatoprazole acid (configuration S) | Mass of KOH |
|---|---|---|---|---|
| 115 g | 47 g | 40.9 g | 4.9 g (10.7% ee) | 8 g |
| / | / | 118.2 mmol | 14.2 mmol | 142.6 mmol |

Results

| No. | Mass of pure antipode (g) | Optical purity (%) |
|---|---|---|
| 1 | 10.4 | −62.9 |
| 2 | 13.9 | +78.9 |
| 3 | 12.9 | −81.9 |
| Mean | 12.4 | 74.6 |

Example 12

Resolution of the Ethylene Glycol Solvate of Tenatoprazole Potassium Salt by Preferential Crystallization at a Scale of 2 liters in an Ethanol/Ethylene Glycol Mixture (80% VV-20% VV)

Variation of $T_{HOMO}$ with the Enantiomeric Excess

The results shown in the following table correspond to steps (iii) to (v).

| enantiomeric excess (% ee) | 0 | 9 |
|---|---|---|
| $T_{HOMO}$ (° C.) | TL = 39.1 | 41.8 |

Conditions Associated with the Kinetics

The conditions below are determined for use during steps (vi) to (ix).

Temperature $T_I=45°$ C.$>T_{HOMO}=41.8°$ C.
Temperature $T_E=32°$ C.
Temperature $T_F=25°$ C.
Temperature ramp=T=f(t)=45½*t (t in minutes) followed by a plateau at 25° C.

Mechanical stirring at 500 rpm, using a twin-blade stirring paddle.

| Temperature (° C.) | 45 | 25 | 25 |
|---|---|---|---|
| t (min) | 0 | 40 | $T_{Filtration}$ |

Initial Conditions

| Mass of ethanol | Mass of ethylene glycol | Mass (racemic) | Mass (configuration S) | Mass of KOH |
|---|---|---|---|---|
| 1200 g | 300 g | 600 g | 85 g (12.4% ee) | 135 g |
| / | / | 1.73 mol | 0.25 mol | 2.4 mol |

Results

| No. | Mass of pure antipode (g) | Optical purity (%) |
|---|---|---|
| 1 | 214.4 | +67 |
| 2 | 111.6 | −93 |
| 3 | 88.7 | +51 |
| Mean | 138.2 | 70 |

Filtration takes place by centrifugation at 5000 rpm with a sock 200 mm in diameter, 100 mm long, and for which the pore diameter of the Nylon filtering medium is 20 μm.

Example 13

Recrystallization of a Harvest in Different Solvents

Examples 13a and 13b describe the recrystallization of harvests in different solvents obtained according to the process described in Example 12. Only the harvests that allow the (−) enantiomer to be obtained were used.

Example 13a 100 g of tenatoprazole potassium salt dihydrate of optical purity=74% ee are recrystallized from 1600 g of ethanol in the presence of 2.6 g of KOH. After total dissolution at 55° C., recrystallization is performed by reducing the temperature to 17° C., and the suspension is then filtered through a Büchner funnel after checking the optical rotation of the mother liquor. The mass of the harvest is 64 g of tenatoprazole potassium salt dihydrate with an optical purity of greater than 99% ee.

Example 13b 100 g of tenatoprazole potassium salt dihydrate of optical purity=74% ee are recrystallized from 1200 g of methanol in the presence of 2.6 g of KOH. After total dissolution at 50° C., recrystallization is performed by reducing the temperature to 10° C., and the suspension is then filtered through a Büchner funnel after checking the optical rotation of the mother liquor. The mass of the harvest is 57 g of tenatoprazole potassium salt dihydrate with an optical purity of greater than 99% ee.

Example 14

Crystal Structures

Examples 14a and 14b present the crystal structures of two enantiomerically pure compounds obtained after performing the process of resolution by preferential crystallization as described in Examples 9, 11 and 12, respectively.

The diffraction intensities were measured with an automatic Smart Apex diffractometer (Brüker).

The structure was resolved with the Saintplus, Sadabs and Shelxs software suites.

Example 14a

The monocrystal of the enantiomerically pure ethanol solvate was obtained by very slow evaporation of a solution saturated with tenatoprazole potassium salt. The characteristics of this phase are as follows:

Monoclinic $P2_1$
a=10.98 Å, b=7.7 Å, c=14.03 Å
α=90.0°, β=101.5°, γ=90.0°

The elementary crystal lattice contains two ethanol molecules in the asymmetric unit.

The value of the Flack parameter is 0.07 (3), which makes it possible to conclude that the molecule has the S absolute configuration.

Example 14b

The monocrystal of the enantiomerically pure ethylene glycol solvate was obtained by very slow evaporation of a solution saturated with tenatoprazole potassium salt. The characteristics of this phase are as follows:

Orthorhombic $P2_12_12_1$
a=7.96 Å, b=10.0 Å, c=25.78 Å
α=γ=90.0°

The elementary crystal lattice contains one ethylene glycol molecule in the asymmetric unit.

The value of the Flack parameter is 0.07 (5), which makes it possible to conclude that the molecule has the S absolute configuration. The optical rotation value measured in ethanol at λ=546 nm is −1.01°.

Example 15

0.29 g (i.e. 5.2 mmol) of potassium hydroxide (KOH) is dissolved in 10 mL of isopropyl alcohol, and 1.52 g (i.e. 4.4 mmol) of racemic tenatoprazole acid are then added. After crystallization at 0° C., the crystalline product is filtered off on a Büchner funnel and analyzed by X-ray powder diffraction.

The product obtained corresponds to racemic tenatoprazole potassium salt monohydrate, which crystallizes in the form of the racemic compound.

Example 16

0.18 g (i.e. 3.2 mmol) of potassium hydroxide (KOH) and 0.96 g (i.e. 2.8 mmol) of racemic tenatoprazole acid are dissolved in a solvent mixture formed by 10 mL of ethanol and 2 mL of propylene glycol. The crystalline product is filtered off on a Büchner funnel and analyzed by X-ray powder diffraction.

The product obtained corresponds to racemic tenatoprazole potassium salt monohydrate, which crystallizes in the form of the racemic compound.

Example 17

0.14 g (i.e. 2.6 mmol) of potassium hydroxide (KOH) is dissolved in a solvent mixture formed by 14 mL of ethanol and 0.4 mL of water, and 0.74 g (i.e. 2.1 mmol) of racemic tenatoprazole acid is then added to the solution. Dissolution is rapid. After stirring for a few hours at 10° C., the crystalline product appears. This product is filtered off on a Büchner funnel and then recrystallized from 1,4-dioxane. The product derived from this recrystallization is filtered off on a Büchner funnel, dried and then analyzed by X-ray powder diffraction.

The product obtained corresponds to enantiomerically pure tenatoprazole potassium salt monohydrate, which crystallizes in the form of the racemic compound.

Example 18

0.48 g (i.e. 8.6 mmol) of potassium hydroxide (KOH) is dissolved in a solvent mixture formed by 10 mL of water and 1.9 mL of N-methylpyrrolidinone, and 2.46 g (i.e. 7.1 mmol) of racemic tenatoprazole acid are then added to the solution. Dissolution is rapid. After stirring for a few hours at 10° C., the crystalline product appears. This product is filtered off on a Büchner funnel, dried and then analyzed by X-ray powder diffraction. The product obtained corresponds to a racemic compound of the potassium salt heterosolvated with water and N-methylpyridinone.

Example 19

Conversion of a Potassium Salt into a Sodium Salt

The enantiomerically pure dihydrate potassium salt (9.6 g) is dissolved in water (50 mL). As the salt is of incongruent solubility, it dissociates partially. Acetic acid (50 mL, 0.5 mol/L) is added in order to neutralize the base and to crystallize the free acid. Next, the crystalline phase is recovered by filtration and rinsed thoroughly with water in order to remove the acetic acid and the potassium.

The mass of acid obtained (S-(−)-tenatoprazole) is 6.57 g, i.e. a yield of about 83%.

1.0 g of S-(−)-tenatoprazole obtained as indicated above is introduced into a 50 mL round-bottomed flask, with moderate stirring and at room temperature, and 1.0 mL of water and then 0.6 mL of aqueous sodium hydroxide solution (5 M) are added.

The reaction mixture is heated at 60° C. for 2.5 hours with stirring to obtain an oily liquid, which is cooled to room temperature. The solvent is removed under reduced pressure at 40° C. on a rotary evaporator. After addition of 6 mL of acetone, with stirring, a pale yellow product is collected by filtration on a sinter funnel, and is rinsed with 2.0 mL of acetone.

After drying at 40'C under reduced pressure for 20 hours, 1.1 g of S-tenatoprazole sodium salt monohydrate are obtained, characterization of which is performed by thermal analysis and by X-ray diffraction.

The invention claimed is:
1. Method for the preparation of an enantiomerically pure Tenatoprazole sodium salt, said method comprising the steps of:
obtaining a tenatoprazole potassium salts, represented by the following general formula:

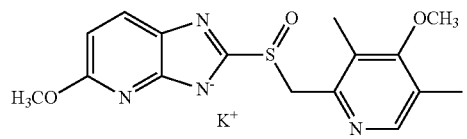

comprising an equimolar mixture of enantiomers of R and S configuration; and
crystallizing said tenatoprazole potassium salts in the form of conglomerates, said salts being selected from the group consisting of tenatoprazole potassium salt dihydrate, potassium tenatoprazole dimethanolate, potassium tenatoprazole diethanolate and potassium tenatoprazole ethylene glycolate;
conducting the resolution of the optical enantiomers of one of the corresponding racemic potassium salts, wherein said resolution is according to a process of preferential crystallization, followed by conversion of one of said optical enantiomers of the potassium salt into the corresponding enantiomer of the sodium salt.

2. The method as claimed in claim 1, wherein said potassium salt is tenatoprazole potassium salt dihydrate, said salt producing an X-ray diffraction spectrum comprising lines at the following inter-reticular distances: 15.16; 8.07; 7.59; 7.23; 7.02; 5.72; 5.55; 5.41; 5.32; 5.05; 4.51; 4.35; 4.29; 4.22; 4.061; 3.926; 3.748; 3.624; 3.539; 3.487; 3.436; 3.392; 3.292; 3.252; 3.222; 3.102; 3.034 (in Angströms).

3. The method as claimed in claim 1, wherein said potassium salt is potassium tenatoprazole dimethanolate, said salt producing an X-ray diffraction spectrum comprising lines at the following inter-reticular distances: 13.79; 6.87; 5.84; 5.44; 4.83; 4.57; 4.31; 3.97; 3.921; 3.865; 3.794; 3.644; 3.56; 3.508; 3.431; 3.393; 3.309; 3.233; 3.116 (in Angströms).

4. The method as claimed in claim 1, wherein said potassium salt is potassium tenatoprazole diethanolate, said salt producing an X-ray diffraction spectrum comprising lines at the following inter-reticular distances: 13.79; 10.73; 9.41; 7.75; 6.87; 6.71; 6.40; 6.25; 5.97; 5.463; 5.377; 5.128; 4.918; 4.711; 4.562; 4.418; 4.020; 3.936; 3.892; 3.855; 3.705; 3.656; 3.623; 3.573; 3.508; 3.460; 3.446; 3.363; 3.302; 3.249; 3.167; 3.129; 3.102; 3.043 (in Angströms).

5. The method as claimed in claim 1, wherein said potassium salt is potassium tenatoprazole ethylene glycolate, said salt producing an X-ray diffraction spectrum comprising lines at the following inter-reticular distances: 12.92; 9.30; 7.89; 7.59; 6.77; 6.05; 5.828; 5.604; 5.409; 5.026; 4.907; 4.657; 4.569; 4.478; 4.295; 4.178; 4.013; 3.972; 3.931; 3.798; 3.692; 3.650; 3.608; 3.543; 3.396; 3.340; 3.300; 3.271; 3.204; 3.148; 3.105; 3.060; 3.013 (in Angströms).

6. The method as claimed in claim 1, wherein said enantiomerically pure Tenatoprazole sodium salt is S-tenatoprazole sodium salt.

7. The method as claimed in claim 1, wherein said enantiomerically pure Tenatoprazole sodium salt is R-tenatoprazole sodium salt.

* * * * *